US006802969B2

United States Patent
Tanimura (10) Patent No.: US 6,802,969 B2
(45) Date of Patent: Oct. 12, 2004

(54) PREPARATIVE CHROMATOGRAPHY SYSTEM AND SEPARATION/PURIFICATION METHOD USING SAME

(76) Inventor: Takenori Tanimura, 2-14-13-306, Atago, Ageo-shi, Saitama-ken (JP)

( * ) Notice: Subject to any disclaimer, the term of this patent is extended or adjusted under 35 U.S.C. 154(b) by 108 days.

(21) Appl. No.: 10/294,018

(22) Filed: Nov. 13, 2002

(65) Prior Publication Data

US 2003/0094415 A1 May 22, 2003

(30) Foreign Application Priority Data

Nov. 19, 2001 (JP) ........................................ 2001-353023

(51) Int. Cl.[7] .............................................. B01D 15/08
(52) U.S. Cl. ..................... 210/198.2; 210/143; 210/656; 210/659
(58) Field of Search ................................. 210/635, 656, 210/659, 143, 198.2; 422/70; 436/161; 73/61.52

(56) References Cited

U.S. PATENT DOCUMENTS

| | | | | |
|---|---|---|---|---|
| 4,604,198 A | * | 8/1986 | Dailey et al. | 210/198.2 |
| 6,296,771 B1 | * | 10/2001 | Miroslav | 210/656 |
| 6,318,157 B1 | * | 11/2001 | Corso et al. | 73/61.52 |
| 6,461,515 B1 | * | 10/2002 | Safir et al. | 210/656 |
| 6,491,823 B1 | * | 12/2002 | Safir et al. | 210/656 |
| 6,641,783 B1 | * | 11/2003 | Pidgeon et al. | 422/70 |
| 2001/0027949 A1 | * | 10/2001 | Safir et al. | 210/635 |
| 2002/0190001 A1 | * | 12/2002 | Petro | 210/656 |
| 2003/0094415 A1 | * | 5/2003 | Tanimura | 210/656 |

FOREIGN PATENT DOCUMENTS

| | | | | |
|---|---|---|---|---|
| JP | 05000204 A | 1/1993 | ........... | B01D/15/00 |
| JP | 08262001 A | 10/1996 | ........... | G01N/30/08 |
| JP | 10282079 A | 10/1998 | ........... | G01N/30/46 |
| JP | 2000081422 A | 3/2000 | ........... | G01N/30/04 |

OTHER PUBLICATIONS

Uretschlager, Andrea, et al; "Continuous seperation of green fluorescent protein by annular chromatography"; Journal of Chromatography A. 908 (2001) 243–250.

Kathleen Mihlbachler et al., Effect of the Homogeneity of the Column Set on the Performance of a Simulated Moving Bed Unit I. Theory, Journal of Chromatography A. 908 (2001, pp. 49–70.

* cited by examiner

Primary Examiner—Ernest G. Therkorn
(74) Attorney, Agent, or Firm—Darby & Darby (57) ABSTRACT

A prepartive chromatography system, and a separation and purification method using the system, are provided for small scale, low cost, efficient multicomponent separation and purification without the drawbacks of conventional separation and purification systems.

The chromatography system and the separation and purification method using it include three or more column units arranged in parallel, and their outlets, from which fractions are taken out, are connected to the same flow path.

13 Claims, 10 Drawing Sheets

PREPARATIVE CHROMATOGRAPHY SYSTEM AND SEPARATION/PURIFICATION METHOD USING SAME

BACKGROUND OF THE INVENTION

1. Field of the Invention

The present invention relates to a chromatography system and a method for separating and purifying a target material from a mixture using the chromatography system.

2. Description of the Related Art

In the separation and analysis of trace components a variety of chromatographic techniques are regularly widely used. In particular, it can be said that the liquid chromatography technique, which can be applied to any sample as long as it dissolves in a solvent, has been established for almost all compounds. As a result, the application of liquid chromatography has been attempted not only for trace amounts of samples on an analytical level, but also for larger amounts of samples using various extensions of analytical techniques (Journal of Chromatography A, 908 (2001) 243–250, JP, A, 5-204, JP, A, 8-262001, JP, A, 10-282079 and JP, A, 2000-81422).

However, where the object is preparation or manufacture, the development of separation technology is currently still in progress.

Where the object is preparation, conventional methods can be broadly divided into the following three techniques.

One method is that in which the size of an analytical column is increased and a large amount of sample is separated all at once. This is extremely easy to understand, but since the usual amount of sample processed in an analysis is a few tens of micrograms or less, even in the case where, for example, a few grams are separated, this is a 100,000 times increase. Therefore, even when considering an analytical column with a size where the volume is in units of mL (or the weight of a packing material is in units of g), since several hundred liters of volume or several hundred kg of a packing material are required, it is not entirely practical.

Of course, in the case of analysis, if the detector can detect the target sample, a small amount of sample can give a margin for resolution, and as long as the detector's sensitivity allows it, the smallest amount of sample is therefore separated. However, when the whole surface area of the packing material is covered with the sample, it is obvious that sample in excess of this cannot be adsorbed on the surface, and for a low molecular weight molecule this is usually assumed at around 30 mg/100 $m^2$. It is assumed that the limit at which a chromatographic separation can be carried out is usually where in the order of one tenth of the surface area of the packing material is covered. Since the surface area of high surface area porous silica gel a packing material is generally around 400 $m^2/g$, the limit for the amount of sample is considered to be around 12 mg/g. Even in this case the ratio by weight of the sample and the required packing material is at least about 100 times. Therefore, even when scaled up, it is necessary to maintain the proportion of the sample relative to the packing material at this value or less all the time during the separation operation and in all parts of the column.

Another reason for a large amount of a packing material being required relative to the sample in liquid chromatography is that, in the chromatography column during the separation process, the part where the actual separation takes place is limited to the part where the target component is. That is, when looked at from the point of view of separation, the part of the column where the target component has already passed through, and the part of the column where the target component has not yet passed through, are not only just occupying space, but also have the negative effect of imposing pressure that opposes the flow of the mobile phase to no purpose, without contributing to the separation. However, in order to carry out a separation between components that only have a small difference in distribution coefficient, a column with a large number of theoretical plates, that is, a sufficiently long column is required, and in the case where a high resolution is required the parts of the column before and after the target component that are not involved in the separation effect at a specific point in time cannot evade the drawback of being inevitably relatively large.

Another problem when applying column chromatography to large-scale fractionation is the issue of what form of column should be used for the packing material, which is several hundred times the amount of the target fraction, and as a second point, even if the required amount of a packing material is decided, what kind of particle size should be used for the packing material.

As is well known, since in chromatography separation is carried out along the length of the column, in order to separate the target component at the required purity from a mixture, it is necessary to have a fixed minimum required length. This length corresponds to the number of theoretical plates needed to provide the necessary resolution, which is expressed as the number of theoretical plates. While the necessary resolution corresponds to the length, the amount processed corresponds to the cross-section of the column. If, as when talking about a normal analytical column, it is possible to load in the order of 0.5 mg of sample for 1 g of adsorbent, since about 1.2 g of a packing material can be packed in a representative column normally used for analysis having a diameter of 4.6 mm and a length of 15 cm , it can be estimated that 0.6 mg of sample can be loaded for a diameter of 4.6 mm. Therefore, by calculation, in order to load 1 g of sample, a column with a diameter of 188 mm and a length of 15 cm is necessary.

When calculating scale-up, the following can therefore be considered.

That is, when there are 10,000 plates in 15 cm, since 1 σ is 100 plates in the vicinity of the outlet, and the maximum concentration is 12 mg/g, the amount that can be processed is calculated as 0.36 mg. Since the calculated value is 0.5 mg when there are about 5000 plates, the calculation shows that the generally held view is substantially correct. For example, when there are 10,000 plates, based on calculation a column diameter of 242 mm is required to process 1 g. That is, a column with a length of 15 cm and a diameter of about 24 cm has to be used. In the same way, it is necessary to use a column with a diameter of 48 cm and a length of 15 cm for 4 g of sample, and a diameter of about 1 m (96 cm) and a length of 15 cm for 16 g of sample.

For example, in the case of a length of 15 cm and a diameter of about 24 cm, in order to make the column longer, when 20 μm particles are used rather than the normally used 5 μm particles without changing the a mount of a packing material , the length becomes 60 cm, and the diameter becomes 12 cm. Moreover, with 80 μm particles, the length increases four times to about 2.4 m, while the diameter becomes 6 cm. A diameter of 6 cm and a length of 2.4 m is quite a practical column size. In this case, when the reduced linear flow rate of the mobile phase is fixed, the linear flow rate at 80 μm is ¹⁄₁₆ of the flow rate at 5 μm, and because the column length is increased by 16 times, it takes 256 times longer. However, even if the reduced linear flow rate is made 20 times, since the reduced plate height (h) is increased only about 4 times, the time required for analysis is after all in the order of 50 times. Therefore, if 10 samples can be arranged and developed on the column, separation can be carried out within 5 times of the processing time per sample.

Moreover, by increasing h 4 times the column length increases 4 times, and since the amount of a packing material also increases 4 times, 4 times the amount is processed in one cycle. However, since the length is increased 4 times, it takes 4 times longer. Therefore, if a large number of 4 g samples can be separated in succession then separation and purification can be carried out with the same resolution during a period of time 5 times that for the analysis of in the order of 0.5 mg of sample.

In a normal chromatography column the length in the direction of progress of the mobile phase is generally longer than the diameter, and the technology is also developing along these lines. Because of this, a technique to uniformly distribute and load a sample on a cross section of a column that has a larger diameter than length, and make the mobile phase flow uniformly across each cross section cannot be said to be completed.

Therefore, in the case where the object is preparation, it is desirable to use a packing material having a larger particle size than that for analysis, and a long column with an internal diameter of a size that is already well used and gives no technical problems.

The second method of separating a large amount that exceeds the limit of chromatography is the method of carrying out separation under the so-called overload conditions. Overload conditions are where separation is carried out under conditions using a high concentration solution such that at least 10%, and depending on the circumstances at least 100%, of the packing material surface area is covered with the material to be adsorbed.

This method is therefore a method where conditions of a constant distribution ratio of the sample between the solid phase and the liquid phase in the separation system, which is a precondition in chromatography, are intentionally disturbed, and it is intended that as a result of the overload conditions chromatographic logic will no longer apply. Therefore, even if a chromatographic result were obtained, this means that a result is obtained that is similar to the result of a chromatographic separation when chromatographic logic does not hold, and the logic is contradicted by the double meaning, thereby proving that chromatographic logic does not hold. Therefore, carrying out separation under overload conditions is a technique that does not follow scientific logic, for which reproducibility is a prerequisite, and that is completely in the trial and error range.

Separation under overload conditions is widely recognized as being by trial and error and having no relation to typical chromatographic theory, and needless to say if all the conditions such as the ratio of the amount of sample to the amount of a packing material, and the types and amounts of components present in a mixture are not identical, the reproducibility cannot be guaranteed. That is, carrying out a separation using a column under overload conditions means that the generalized rational logic of chromatography cannot be applied, and it cannot be said to be scientific. Furthermore, as well as it being based on trial and error, the large store of knowledge relating to chromatographic separation cannot be applied. That is, it can be said that the above-mentioned method, other than the fact that it employs a column used for chromatography, is an operation, unlike chromatography, to which much existing knowledge cannot be applied.

The third method is the so-called 'simulated moving bed' method (Journal of Chromatography A, 908 (2001) 49–70). This is a method in which a mixture is continuously separated into two parts at the boundary of specific distribution coefficients, and the object is fundamentally different to the chromatographic type method in which a mixture containing a large number of components is separated into the individual components. However, it is considered to be an extremely effective method for separation where there are originally only two components, as in the case where each enantiomer of an optically active material is separated.

This method attempts to exhibit, between a solid phase and a liquid phase, the same effectiveness as a countercurrent separation and extraction method using two immiscible liquid phases. When there are two liquid phases, the two liquids can be made to flow in a countercurrent state, but in the case where one is a solid, in general the solid cannot flow. Accordingly, the simulated moving bed was devised in order to get a similar effect to that which would come from the case where the solid phase flowed.

However, since this was originally for making a countercurrent state, the object thereof was to separate a mixture into two components as above, and it is not possible to take out one component from a mixture by this method. It should therefore be considered to be a technique that is different from chromatography, which can efficiently separate one component from a multi-component system.

Furthermore, there is the so-called 'heart-cut' method by column switching, in which the object is analysis, and which is related to a multiple-column switchover technique. This is a technique in which, by using a pretreatment column so as not to introduce unwanted fractions into an analytical column system, contamination of the analytical column can be prevented. For example, this method is used not only when a component other than the target of analysis is introduced into an analytical column, thus causing contamination, but also when a component that is more strongly adsorbed on the packing material than the material to be analyzed and cannot be readily eluted after the analysis is completed is present in the mixture, with the object of shortening the long time that is necessary for washing and regenerating the column for the next analysis. Because it is only the intermediate necessary fraction that is taken out and injected into the analytical column, this technique, referred to as the 'heart-cut', is widely used.

This technique is considered to be a pretreatment technique in which the whole of a column required for a separation is divided into two, one part is separated, and only the required fraction is taken out. In this technique, achieving efficiency by introducing a plurality of samples into the second half of the analytical column is not considered; rather, the main point is that efficiency is achieved by washing and regenerating the first half of the column while separation is being carried out on the second half of the column, and since the first, pretreatment, half of the column is regenerated along with completion of analysis by the analytical column, advantages can be recognized from the point of view of being able to immediately inject the next sample for analysis, and from the point of view of being able to avoid unnecessary contamination of the analytical column by components of the mixture. However, the application for multiple analyses with columns having the same high performance using a plurality of pretreatment columns is not considered. Therefore, in this technique, reducing as much as possible a packing material that does not take part in the separation at a specific point in the time during the above-mentioned operations, that is, parts of the packing material In which no sample is present at a specific point in the time, which is one of the wasteful aspects of chromatography, and keeping as much as possible of the packing material of the system always involved in separating the sample, is a point of view that is lacking.

The above-mentioned standpoint of the 'heart-cut' method is rather common from the standpoint of the object being analysis. The reason for this is that since there is little sample in analysis, by minimizing the amount of a packing material required, and also necessarily reducing the amount of mobile phase solvent, it is necessary for the measurement of the concentration not to dilute a minute amount of the material to be analyzed, and also, because the original amount of a packing material required is small, even when it is expensive such an amount can be used if necessary.

As hereinbefore described, up to now attempts have been made to make a variety of systems and methods for pre-parative chromatographic separation and purification, but all of them have problems from the point of view of scale, cost or efficient performance.

BRIEF SUMMARY OF THE INVENTION

The object of the present invention is therefore to provide a preparative chromatography system for efficient separation and purification with a small scale and low cost, without the drawbacks of conventional separation and purification systems, and a separation and purification method using same.

The inventors of the present invention, while carrying out an intensive investigation taking into account the above-mentioned problems, focused attention on the object of the preparation being primarily the amount and purity of the target component, and with regard to fractionation for the preparation, rather than taking out, with high purity, multiple components in a mixture, the many cases where the object is to take out, with high purity, one specific component in a mixture or a few components. The inventor of the present invention found out that, after obtaining a plurality of fractions of the same components from a purifying pretreatment of a mixture, by additional purification and separation if necessary by putting the plurality of fractions of the same components on the same column with different timings, it is possible to separate mainly one component with the purity of the degree achieved with high performance chromatography, or the purity exceeding that. Furthermore, by eluting the separated component peaks from the column with as short a time interval as possible, means to increase the amount processed per unit time was also found, and the present invention has thus been completed.

That is, the present invention relates to a chromatography system comprising three or more column units arranged in parallel, wherein outlets from which fractions are taken out are connected to the same flow path.

Furthermore, the present invention relates to the above-mentioned system further comprising a column unit having a resolution required to separate and purify a target material, the column unit being connected to the downstream side of each of the column units arranged in parallel.

Moreover, the present invention relates to the above-mentioned system wherein the column unit connected to the downstream side of each of the column units arranged in parallel comprises three or more column units linked in series with each other.

Furthermore, the present invention relates to the above-mentioned system wherein the column units linked in series with each other comprise 10 or more column units.

Furthermore, the present invention relates to the above-mentioned system wherein the injection inlet of each of the column units arranged in parallel is connected to a same supply flow path.

Moreover, the present invention relates to the above-mentioned system wherein a valve is provided in the supply flow path in order to inject a sample with a time interval between each of the column units arranged in parallel.

Furthermore, the present invention relates to the above-mentioned system wherein a valve and a pump to enable fractions taken out from each of the column units arranged in parallel to be sequentially introduced into the column unit connected to the downstream side carry out the introduction while maintaining a time interval in order that a peak of a purified target component and peaks of impurities do not overlap in the column unit connected to the downstream side.

Furthermore, the present invention relates to the above-mentioned system wherein it further comprises a valve and a pump having, between columns of the column units linked in series and purifying the target component, a flow path system for removing separated impurities and a flow path system for introducing a pure mobile phase corresponding to the volume of the mobile phase removed.

Moreover, the present invention relates to the above-mentioned system wherein it further comprises a computer system that automatically controls one, or two or more of sample injection, valve flow path switchover, and pump operation and stopping.

Furthermore, the present invention relates to the above-mentioned system wherein it is used for separation and purification of a biologically active material from a mixture containing the biologically active material.

The present invention also relates to a method for the separation and purification of a target material from a mixture comprising, in a system comprising column units arranged in parallel and a column unit connected to the downstream side of these column units, supplying samples comprising substantially identical components to each of the column units arranged in parallel with different timing, taking out the eluted fractions, and then introducing the fractions to the column unit connected to the downstream side for further purification and separation.

Furthermore, the present invention also relates to the above-mentioned method wherein the introduction of the fractions eluted from the each of the column units arranged in parallel to the column unit connected to the downstream side is carried out while maintaining a time interval in order that a peak of a purified target component and a peak of an impurity do not overlap in the column unit connected to the downstream side.

Moreover, the present invention also relates to the above-mentioned method wherein the column unit connected to the downstream side comprises serially linked column units, and separation of the impurity is carried out between target component peaks by removing the separated impurity and introducing pure mobile phase corresponding to the volume of the mobile phase removed between columns of the serially linked column units.

DETAILED DESCRIPTION OF THE INVENTION

Advantages of the preparative chromatography system and the separation and purification method of the present invention are described below.

The system according to the present invention, in summary, carries out a purification by injecting a mixture containing a target component at suitable intervals into columns arranged in parallel, taking out only those fractions containing the target component and impurities that are difficult to separate therefrom and, if necessary, introducing these sequentially into serially linked column units that have the necessary resolution, and this mode can also be called a system for consecutive chromatography.

The parallel columns are for carrying out a separation with the object of a heart-cut by removing unwanted fractions and introducing only the required fractions to the serial columns. In the sample separation process the direction of movement of the mobile phase in the parallel columns is therefore always fixed.

First of all, in the chromatography system according to the present invention, from the point of view of as much of the packing material as possible always being related to the sample separation in the system, since a large proportion of the solvent is also directly involved in separation in the system, it is superior to ordinary chromatography from the point of view of effective utilization of a solvent as well as a packing material. This can be said to be a large advantage in the case where the object is a preparation requiring a large amount of a packing material, and particularly in the case where a packing material or a solvent for which the cost cannot be ignored is used.

If, using the system according to the present invention, two or more fractions containing the target component are successively introduced to the serial columns from the parallel columns with a suitable staggered timing, when the separated target component is eluted from the serial columns it is possible for it not to overlap an impurity separated from the target component. Furthermore, when it is desired to purify and take out two or more components, two or more series of serial columns are connected to the parallel columns, and one of the components can be separated and purified from each of the series.

Since one of the objects of the present invention is to provide a method for taking out mainly one component from a multi-component mixture of three or more components and the simulated moving bed can continuously separate a mixture into only two components, said method is different therefrom in its objects and constitutions. That is, since in the simulated moving bed, when the distribution coefficient of the target component is other than the largest or the smallest among the distribution coefficients of the multiple components when they are arranged in order of the size, the required component cannot be isolated, and two operational cycles are usually required, whereas in contrast in the system according to the present invention, since it is chromatography, there is a point of difference that isolation is possible with one operational cycle, this clearly also being an advantage.

Furthermore, compared with the separation process under the so-called overload conditions, since the distribution coefficient between the stationary phase and the mobile phase does not go beyond the concentration range that can be considered to be constant from the point of view of making use of knowledge and experience obtained from chromatography where the object is analysis, the method is clearly superior.

That is, compared with the separation process under overload conditions where the conditions must always be determined by trial and error, since the reproducibility is far better, there is an advantage that an automatic continuous operation is possible.

Furthermore, as described above, in order to deal with a large amount of sample using a chromatographic technique in which the resolution is conventionally excellent in the length direction of the mobile phase, techniques have been developed using a column having a large internal diameter that approaches the length or a tablet-like column having an internal diameter that exceeds the length. However, even in this case, remains the drawback that the higher the resolution of the column used, the higher the ratio of the whole column a packing material necessary to the part where the separation of the target sample is actually taking place, so that there are many parts where the target sample is not present at a specific point of time during operation. For example, in a column with 900 theoretical plates, the proportion of the target sample present, even in the vicinity of the outlet where the proportion is the greatest, is not more than about 20% in the case where the sample width is 6 σ, or 6 times the standard deviation. Furthermore, in a 10,000 plate column, which is usually considered to have high performance and is necessary when a separation is considered to be difficult so that a separation by chromatography is needed, the proportion is 6%, in a 40,000 plate column it being only 3%.

Therefore, compared with the conventional process, the present invention is characterized in that the higher the performance of the column, the smaller the relative proportion of the part of the column where there is no sample is. This particularly is a big advantage in the case where an expensive a packing material is required, or in a purification on such a production scale that a large amount of a packing material is required.

In contrast to this, in the system of the present invention, if, for example, a sample is injected in such a way that there is an 8σ interval at the column outlet, and a 10,000 plate column is used, in the vicinity of the outlet the part of the column where there is no sample is 25% and the part where the target sample is present is 75%, the column being used effectively. Moreover, since with this ratio an interval between peaks of 2σ for a peak width of 6σ is planned, this relationship at the outlet of the column is not related to the separation efficiency of the column. Furthermore, when a high resolution column, that is, a column with a large number of theoretical plates is used, since the peak width is naturally broader than when using a column with low resolution, that is, with a small number of theoretical plates, when the injection is at 8σ intervals and the number of theoretical plates is N, the interval on the column is $$8\sqrt{N}, \quad \text{[Equation 1]}$$

that is, the time interval is $$\frac{8t_R}{\sqrt{N}}. \quad \text{[Equation 2]}$$

Since the retention time $t_R$ is proportional to N, the injection interval on an SC system is proportional to the square root of N.

Therefore, the sample injection interval is determined by how many theoretical plates the column has in order to achieve the purity required of the purified target sample. However, the processing time per peak is proportional to the square root of the number of theoretical plates in the present method when the flow rate of the mobile phase is constant, and since in normal chromatography it is proportional to the number of theoretical plates, it is clear that the present method is advantageous.

As is known well, in separation by chromatography, each component to be separated moves on the column at a speed which is determined according to distribution coefficients, which are physicochemical constants intrinsic to each component between the stationary phase and the mobile phase in the system. This means that components present in the mobile phase at a high percentage move more quickly than components at a low percentage. By this process of movement the countess molecules constituting each component spread out to a fixed width centered on an average speed. The width of this spread relative to the distance moved is narrow for a column with a high separability and is broad for a low-separability column. According to the chromatographic theory, under ideal conditions the shape of the elution curve of a sample is a normal distribution. In practice also, as a result of advancement in technology, it is not difficult at present to obtain elution conditions that can be considered as achieving a separation that follows the theory.

Plate theory explains the width of this spread. This theory divides the column in a direction perpendicular to the direction of flow of the mobile phase into a large number of imaginary equally sized sections. Since the amounts of stationary phase and mobile phase are uniform in each of the sections, the proportions of the sample distributed in each of the sections are also identical.

The column can therefore be considered as being one in which such imaginary sections extend in series, one of these sections being called one theoretical plate.

The following equation for the resolution defines the extent of separation of components that are difficult to separate.

$$(I) \quad Rs = \frac{\sqrt{N}(\alpha-1)(\overline{k'})}{2(\alpha+1)(\overline{k'}+1)} \quad \text{[Equation 3]}$$

Here, Rs is the resolution, N is the number of theoretical plates, $\alpha(=k'_2/k'_1$; $k'_1$ and $k'_2$ are capacity factors of component 1 and component 2) is the separation factor, k' is a capacity factors, and $\overline{k'}$ is the mean of $k'_1$ and $k'_2$.

A resolution of 1 is usually the target, and a resolution of 1.5 is complete separation.

To increase the resolution, it is necessary to increase the separation factor or the number of theoretical plates in the above equation, or to maintain the mass distribution ratio k' relatively large. In usual purification requiring chromatography, it is often the case that the separation factor is dose to 1. Since the separation factor is the ratio of capacity factors, it is a physicochemical constant and can be determined by choosing the stationary phase and the mobile phase. Since the number of theoretical plates is the number of sections described above, it increases as the column becomes longer. By changing the composition of the mobile phase, k' can be adjusted over a considerable range.

However, since components that are difficult to be separated from each other also often have similar physicochemical characteristics, because their capacity factors change in the same way with a change in the mobile phase, it is often difficult to change the separation factor to a large extent. Therefore, increasing the number of theoretical plates, that is, lengthening the column, is an easily controlled condition for technically solving the separation of components hard to be separated from each other. In separation by HPLC, since there are usually ten or so thousand plates, even if the object is separation and purification, taking 10,000 plates as an example, when the above-mentioned sample width is dispersed with a normal distribution in the vicinity of the outlet of the column, 6σ corresponds to a width of about 600 plates. In this case, therefore, even in the vicinity of the column outlet the sample uses only ¹⁄₁₆ of the column.

If the column has sufficient resolution efficiency, this spread can be considered as an approximately normal distribution, and a column used in chromatography usually satisfies these conditions.

Although the object of the present invention is preparation, from the point of view of separating a specific component with high purity from a mixture, it is identical to the case where the object is analysis. Therefore, after the heart-cut of specific components from a large number of samples, if they are fed to a separation column system with the shortest necessary interval, the number of samples that can be processed per unit time increases. It is therefore effective in the case where a large number of similar samples are present and there are few components to be analyzed.

Since the object of a PC column section of the system relating to the present invention is not purification and separation but taking out material that is retained in the packing material or has an elution time in a specific range, a chromatography column with low resolution, that is, a short column, can be used. Because of this, sample injection, and column washing and regeneration etc. are carried out on a short column system, and high pressure operations employed in the usual HPLC are unnecessary. Therefore, since the switchover of complicated flow paths as in Example 1 is carried out at low pressure, an advantage of the chromatography system of the present invention is that high pressure valves are not required for flow path switchover.

Since inherently highly pressure resistant 6-way valves, such as valves sv1 to sv4 in Example 1 and Example 2 below, are suitable for the introduction of the wanted fractions to SC column units, which are the only ones that require high pressure, it is not wasteful as a system.

Another advantage of the present invention is that the efficiency can be measured by the frequency of sample processing per unit time, and not by the time for one sample as in normal chromatography. Of course, if the frequency of sample processing per unit time increases, the time for processing one sample also naturally decreases, but when paying attention to one specific sample, it is not possible to avoid the processing time being considerably longer. However, even if it takes time to separate one specific sample, since a large number of samples are separated concurrently, separation conditions can be chosen that in the conventional method require a long time, which is disadvantageous or impossible.

When columns with the same number of theoretical plates are used in a chromatographic separation, as can be easily understood from Equation (I), if other conditions are the same, then when k' is larger the resolution improves. Taking time into consideration, separation is usually carried out under conditions of k'=from 3 to about 10, and carrying out a separation with k'=around 2 is unusual. However, when identical columns are used, the resolution per unit time is a maximum for k'=2, and does not greatly change for k'=around 1.4 to 2.9.

In the usual process, in order to complete the separation in a given time, accompanying the lengthening the column and the increase in the number of theoretical plates, the speed of the mobile phase must be increased, and as a result the liquid feed pressure rises. However, there are limits to the liquid feed pressure of the pump and the pressure resistance of the packing material. Furthermore, since due to the particle size of the packing material the mobile phase flow rate cannot become slower than a certain degree, there is a limit to lengthening the column while reducing the flow rate. Therefore, choosing elution conditions in the vicinity of k'=2, which gives a good resolution per unit time, is not always possible in the usual process.

Because the number of processes per unit time is an issue in the present invention, k' can be chosen from a range that gives the best resolution per unit time. In the same way as for the packing material, the mobile phase in the columns also carries out elution of sample, pre-development of sample and removal of unwanted components, and washing and conditioning of the column in the parallel column unit PC columns, and since there are few parts in the SC units where the sample is not present, it is possible to minimize the total mobile phase unrelated to the separation.

The present invention has been completed as a result of exploring the extent to which already established analytical techniques are applicable for large scale samples. The present invention makes possible a method that can prepare a purified material having extremely high purity on a small manufacturing scale, and is extremely effective when applied to biologically highly active pharmaceuticals, intermediate compounds for synthetic research, etc.

Furthermore, by using a column packed with a packing material that has selectivity for enantiomers, the present invention is naturally suitable for use in the separation of two components such as in the separation of each enantiomer from an enantiomer-containing mixture.

MODES FOR CARRYING OUT THE INVENTION

Embodiments of the system and method in accordance with the present invention are explained below using diagrams.

The preparative chromatography system in accordance with the present invention is typically formed from a plurality of parallel column systems arranged in parallel that take out mixture fractions containing the target component, and a column system that purifies the required part in the fractions thus taken out.

Figure 1:
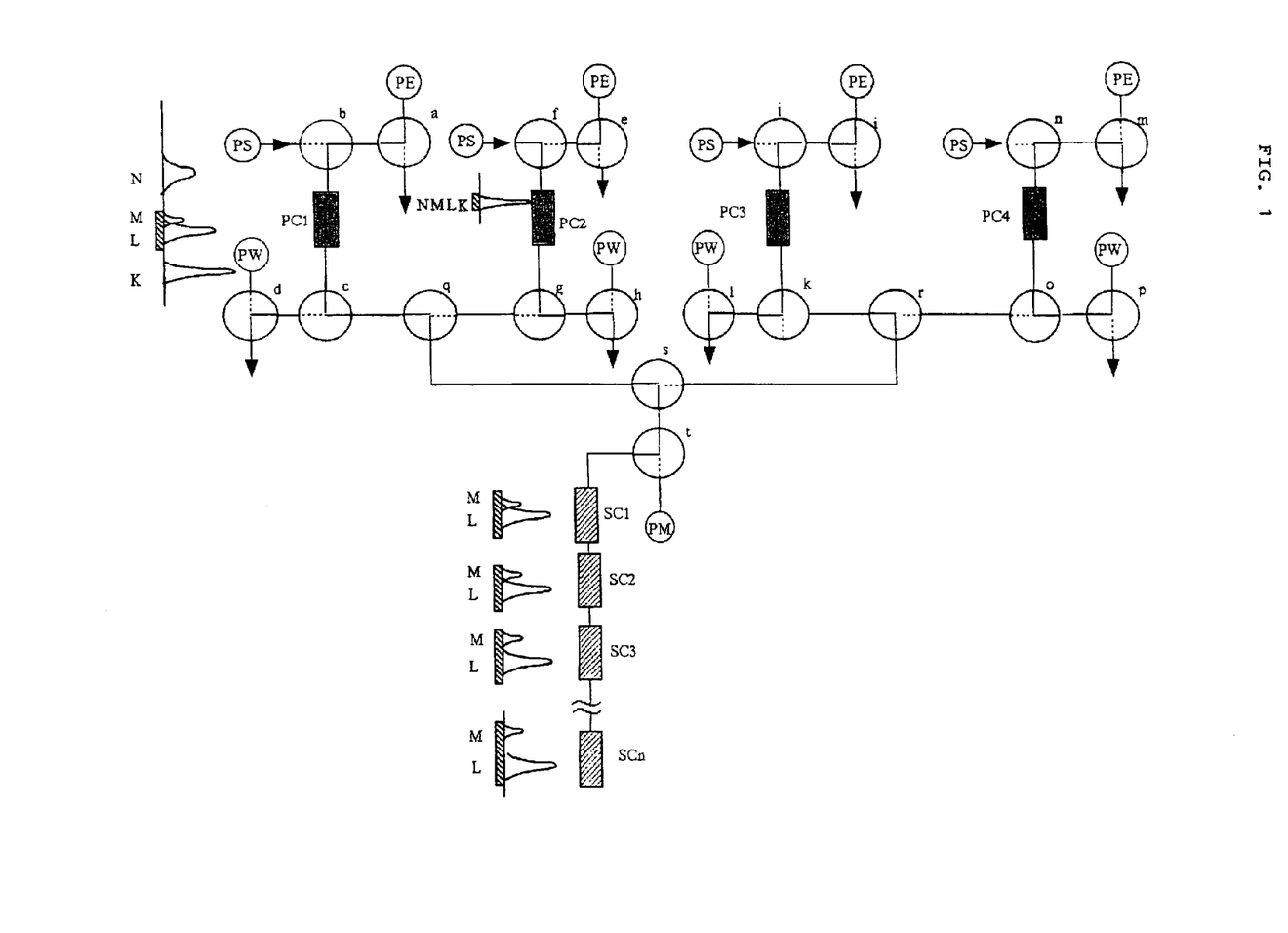
FIG. 1 is a schematic diagram showing one embodiment of the chromatography system according to the present invention.

In FIG. 1, columns PC1, PC2, PC3, . . . PCn are parallel columns arranged in parallel for the heart-cut taking out of target fractions, and SC1, SC2, SC3, . . . SCn are serial columns arranged in series for purifying a target component. These serial columns are set up in common to the parallel columns, and function as shared columns. PS is a sample injection pump, PE is a pump that feeds a mobile phase to a parallel column, PM is a pump that feeds a mobile phase to a serial column, and PW is a pump that feeds a mobile phase for washing to a parallel column. Furthermore, a to t are 3-way valves that switchover flow paths for feeding the mobile phase as required to each of the columns. In addition, the outlets of the plurality of parallel columns from which fractions are taken out are combined and connected to the injection inlet of one shared column.

An example of taking out L from a sample mixture containing components K, L, M, and N is now explained.

First, the sample is added to heart-cut column PC1, the mobile phase is made to flow to elute K. Next, when the fraction containing the target component L, and M that is difficult to separate from L and elutes from PC1 together with L (hatched area in FIG. 1: called the L,M fraction below) is eluted from PC1 a flow path is switched over, and this fraction is guided to the purification column unit SC1. After this fraction is eluted from PC1 the flow path is returned to the original one, and fractions containing components eluted later than M are eluted outside the system from PC1, and are not introduced into an S system unit for purification. The mobile phase is made to flow on an S column so as to move the L,M fraction introduced into the S unit. Next, after a fixed interval, in the same way as with column PC1, the L,M fraction is taken out from PC2 and introduced into the S unit. By carrying this out in succession with PC3, . . . PCn, L,M fractions are introduced into the S unit at fixed intervals.

The L,M fraction moving on the S unit column gradually separates, and divides into peaks for each of L and M.

When L and M are sufficiently separated, if the L and M fractions are collected separately at the outlet of the column unit, purified L can be obtained at constant intervals. After elution of the L, M fraction from columns PC1, PC2, . . . ; washing of the columns is carried out by a suitable method such as (1) washing with a solvent with strong eluting power, or (2) making slightly more of the mobile phase than was used to elute the LM fraction flow in reverse into the column outlet, thereby washing out from the inlet N and later components that elute more slowly. In the case of (2), an efficient way of washing is, for example, to wash the first quarter of a PC column using the same eluant but to the opposite direction to that of the elution of the sample all through the period during which the sample passes the latter three quarters of the column. Thus, the PC column can almost completely be regenerated to the extent that it has no movable substances remaining therein since the first quarter has been subjected to washing three times longer than the elution. In the case of (1), by arranging conditions thereafter by equilibrating with the original mobile phase using a suitable method so that another sample can be injected, it can be used repetitively at certain intervals.

In order to inject the L3M fractions at fixed intervals into the SC unit, after injecting the fraction, since the next L3M fraction must be in the vicinity of the outlet of the next column of the PC unit after a fixed time, the PC unit columns are repeatedly put successively into states in which the L,M fraction is injected into the SC unit, the L,M fraction is developed, the residue is washed, and they are ready for sample injection. Depending on the type of the sample, these stages can be omitted or shortened, but in order to enable to carry out consecutive operation in a stable manner it is preferable that there are at least 4 columns in the PC unit.

In the above manner, by the use, in rotation, of the PC unit columns arranged in parallel, and by purifying the required fraction in the sample to the required purity by intermittently injecting it into the SC unit columns linked in series and having the required resolution, the target fraction can be separated. By linking in series in the SC unit only the number of columns required to give a length equivalent to the number of theoretical plates required for separation and purification, a suitable separation and purification can be carried out. That is, if necessary, separation and purification is carried out on at least 4 linked columns. For example, if 10 columns of a thousand theoretical plates are used, a separation efficiency of 10,000 plates can be obtained, which is preferable.

In addition to an outline of the embodiment in FIG. 1 as given above, a supplementary explanation is now added.

As above, PC1 to 4 are parallel heart-cut columns, SC1 to n are serial purification columns, and PE, PS, PW, and PM are respectively the parallel column elution pumps, sample injection pumps, washing pumps for regeneration of the parallel columns, and the main elution pump for the serial columns. Furthermore, a, b, c, . . . t are 3-way valves for switching over the flow paths, the solid lines in FIG. 1 denote flow paths in use, the solid lines in the figures of 3-way valves are represented by a, b, c, . . . , and in a', b', c'. . . dotted lines denote the positions of the alternate flow paths used.

In FIG. 1, the operation is further explained in a case, as an example, where L is taken out from a mixture comprising, the order of elution from a column, are K, L, M, and N, in which L and M are hard-to-separate components.

First, the sample is injected onto column PC1. At this point, PE is stopped, PS is operating, and the valves are in positions b', c', and d. After injecting the sample, PS is stopped, PE is operated while the eluant flows with valve positions at b, c', and d, K is eluted through d, and that state is maintained until just before L starts to elute. When the valves are put to the positions a, b, c, q, s, and t as in FIG. 1, fraction L accompanied by M is introduced into SC1. After introducing L into SC1, PE is closed so as to avoid putting in unrequired components as much as possible, and PM is operated with valve position t'. Thereafter PW is operated with the valve positions at a', b, c', and d', thereby carrying out washing of PC1. This Is a state corresponding to PC 4 in FIG. 1. Fraction L introduced onto SC1 moves on the column, and there is no sample in the part of SC1 in the vicinity of its entrance. The thus predetermined mobile phase is made to flow, leaving a suitable interval. Thereafter, fraction L of the next sample is introduced onto SC1 from PC2 which has been prepared as described below.

The next sample is introduced onto column PC2 with suitable timing during the above operation with the valve positions f, g, h as shown in FIG. 1. Similarly, after injecting, the valve position is changed to f, and the sample is similarly made to move on the column until just before L is eluted. PC4 has an equivalent flow path system to the above-mentioned washing state for PC1, and PC3 shows a flow path state of equilibrium by the elution solvent after washing. By means of such a concept, by successively processing at suitable staggered timing, the fraction L which it is desired to purify can be successively injected into the SC column system at suitable intervals.

A case where impurities such as m and M, eluting closely to the target component L on either side thereof, are present in the sample introduced into the SC system, and are too close to the samples one before or one after injected at fixed intervals is now explained.

Figure 2:
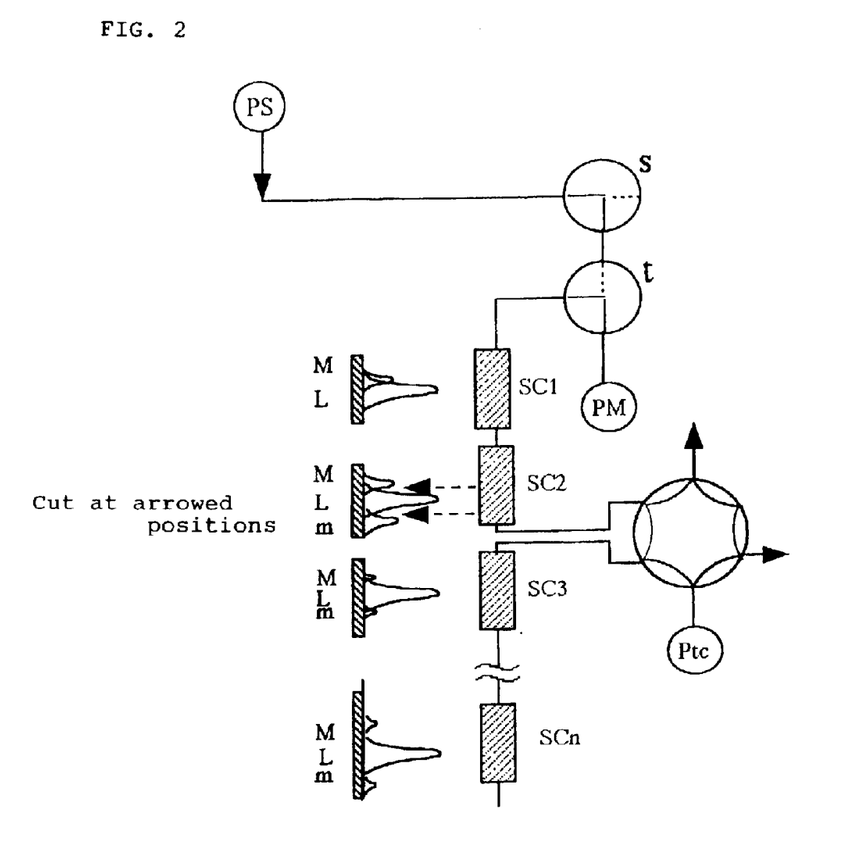
FIG. 2 is a schematic diagram showing another embodiment of the chromatography system according to the p resent invention.

In this case, as shown in FIG. 2, a pump (Ptc) and a valve connected between the serial columns are used. For example, among impurities which are up until then partially separated, the target component L is heart-cut and the component m is taken out of the system at the outlet of SC2 by means of the flow path inserted between SC2 and SC3, which are connected by the pump and the valve. After this, an amount of fresh mobile phase corresponding to the amount or more of the mobile phase containing component m just taken outside the system is made to flow into SC3, and when next component L starts to elute column SC2 and column SC3 are reconnected, and next component L is introduced into the SC3 that follows.

When component L is completed component M is again taken out from the system, and a similarly corresponding amount or more of fresh mobile phase is made to flow into the SC3 system. The necessary interval between the peaks of component L is kept in subsequent columns as a result of this operation, impurities adjacent to the foot of the peak of component L are removed, and purification of the fraction containing component L can be continued. In this way, components m and M separated from the peak of component L can appropriately be removed even during the course of the purification.

With reference to a shaving process carried out by recycle chromatography in this way, the reverse can also be applied. That is, in accordance with the shaving process, with regard to the case of FIG. 2, in the same way as above, components equivalent to m and M that have been divided and purified from the mixture peak can be taken out.

Figure 3:
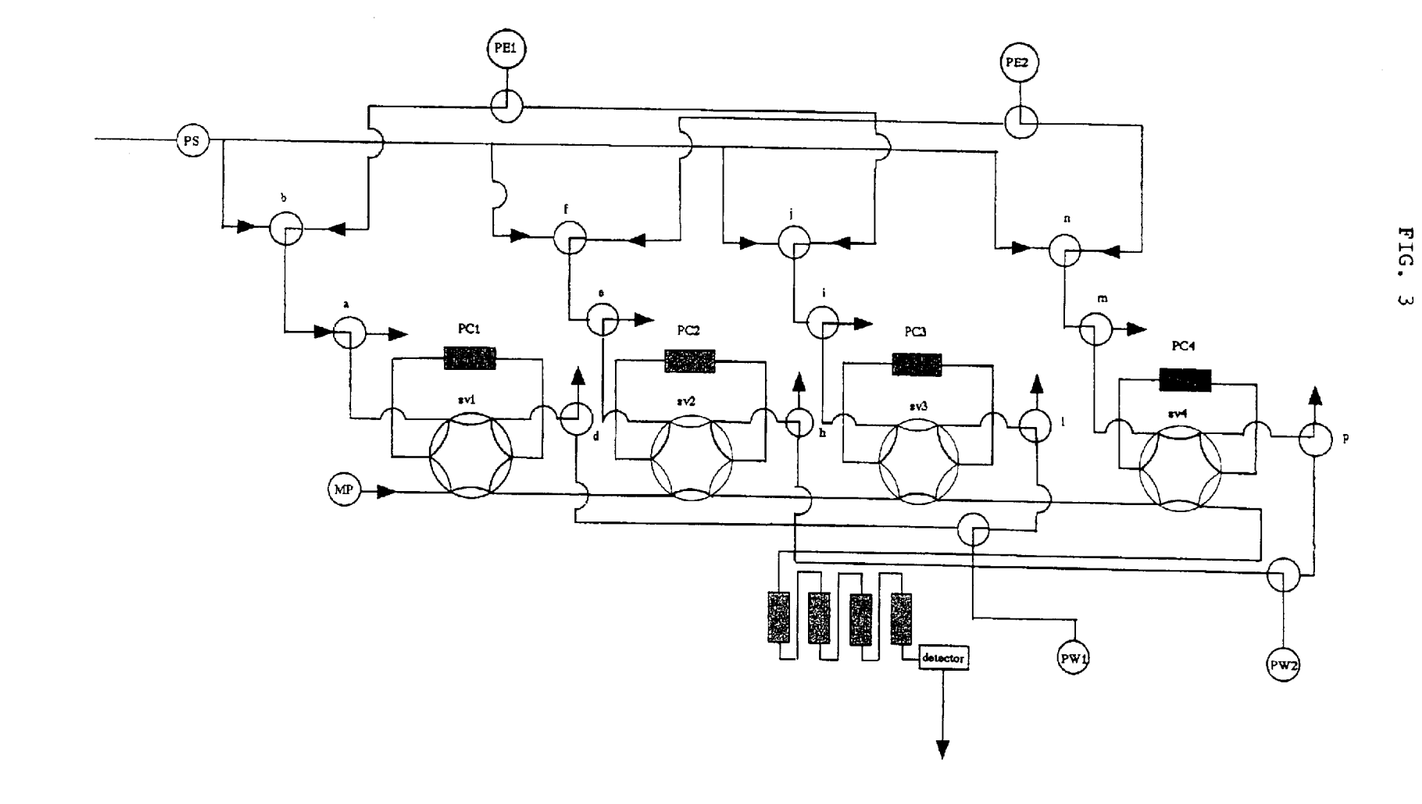
FIG. 3 is a schematic diagram showing one example of the chromatography system according to the present invention.

As shown in FIGS. 1 to 3, as well as operating and/or stopping a large number of pumps at determined times, the flow paths of in excess of as many as 20 valves are switched over and continuously repetitively operated, which exceeds the limit of manual operation, so that in practice automatic control is required. If the solvent and sample solution are continuously supplied thereby, since continuous operation for 24 hours a day is possible, even if the amount purified in one cycle is 1 g, and the interval between sample injections is 15 min, about 100 g can be purified in one day, and it can be calculated that 1 kg of purified material can be obtained in 10 days.

Moreover, by using a column with a large internal diameter, it is possible to purify up to about 100 kg in one year, and if column technology improves even larger amounts can be processed.

Completely independent sway valves are shown in FIG. 1 for the purposes of explanation, but since several flow paths can be switched over at the same time and, furthermore, the pumps also are operated and stopped, they can be shared. In particular, in order to increase the resolution, the flow paths including the serial columns might employ a column with a large overall number of theoretical plates, that is, a large number of serially linked columns, and in this case the flow pressure of the mobile phase also increases. Therefore, valves that can resist high pressure must also be used in these flow paths and, for example, a pressure resistant 6-way valve can be used.

Examples

The present invention is explained further in detail by means of examples, but the present invention should not be construed as being limited thereby in any way.

(Example 1) Separation and Purification of a Chemical

As shown in FIG. 3, 4 parallel column units, 4 serial column units, and 4 6-way valves were used. In the schematic drawing shown in FIG. 1, the sample injection pump PS was common to each PC column, the mobile phase liquid feed pumps were also used in common for columns PC1 and PC3, and for columns PC2 and PC 4, in the same way the column washing pumps were also used in common for columns PC1 and PC3, and columns for PC2 and PC 4, and the valves used for introducing the required component from the parallel columns to the serial columns were replaced by 6-way pressure resistant valves (sv1 to 4). Spherical ODS silica gel with a particle size of 50 $\mu$m was used as the packing material, the column having an internal diameter of 1 cm and a length of 30 cm.

PE1 and PE2 were mobile phase feed pumps for the respective parallel columns, MP was the mobile phase feed pump for the serial columns, PW1 and PW2 were feed pumps for mobile phase for washing the respective parallel columns, and a to p were 3-way valves for switching over the flow paths for feeding the mobile phase to each of the columns.

Figure 4:
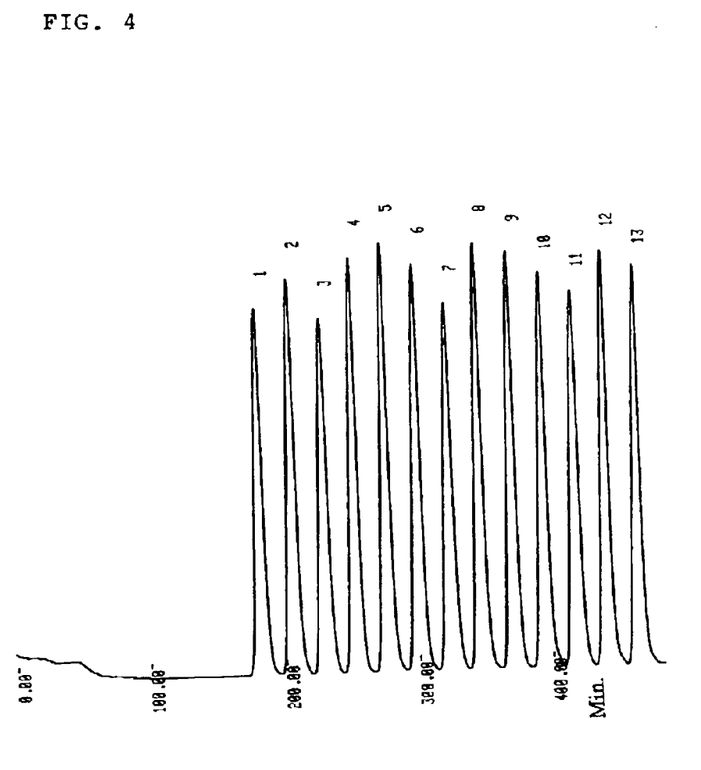
FIG. 4 is one example of the result of chromatography according to the present invention.

FIG. 4 shows one example of a chromatogram using the flow paths of the present example.

The mobile phase was methanol—water 70:30, the flow rate was 1 m/min, and detection was carried out by absorbance at 280 nm. The sample was propyl para-hydroxybenzoate. Because there were 4 parallel columns, a case of a chromatogram is shown (FIG. 4) where sample injection was carried out for three and one quarter cycles, that is, 13 times, at intervals of 23.52 min.

It was confirmed that elution of the sample was carried out as expected.

(Example 2) Separation of a Purified Component from a Natural Product

Figure 5:
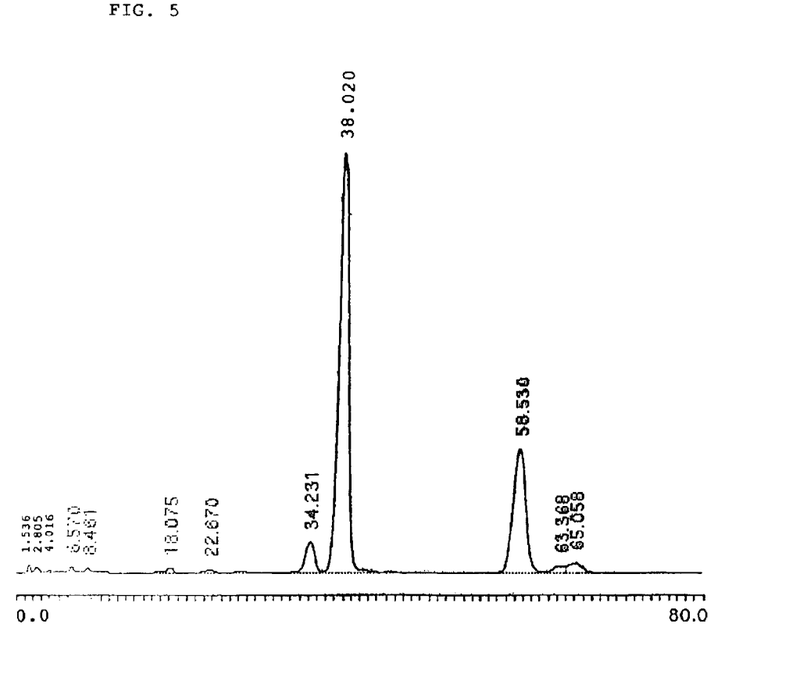
FIG. 5 is a chromatogram of an analysis of the red chilli pepper extract use d in Example 2.

Example 1 confirmed the basic performance using a chemical. This is an example where the present method was applied to the separation of a purified component from a natural product. The example shown here is a case of the separation of capsaicin from red chilli pepper. First, by extracting capsaicin under conditions so that as few impurities as possible were present, a fraction with the composition shown in FIG. 5 was obtained.

Using this sample, 4 parallel columns as in Example 1, and 10 serial columns for giving a separation efficiency of substantially 10,000 plates were used. The column size and a packing material were the same as in Example 1, and the separation efficiency per column was about 900 plates. The mobile phase was acetonitrile—water 57:43, and a flow rate of 2 m/min was used.

Figure 6:
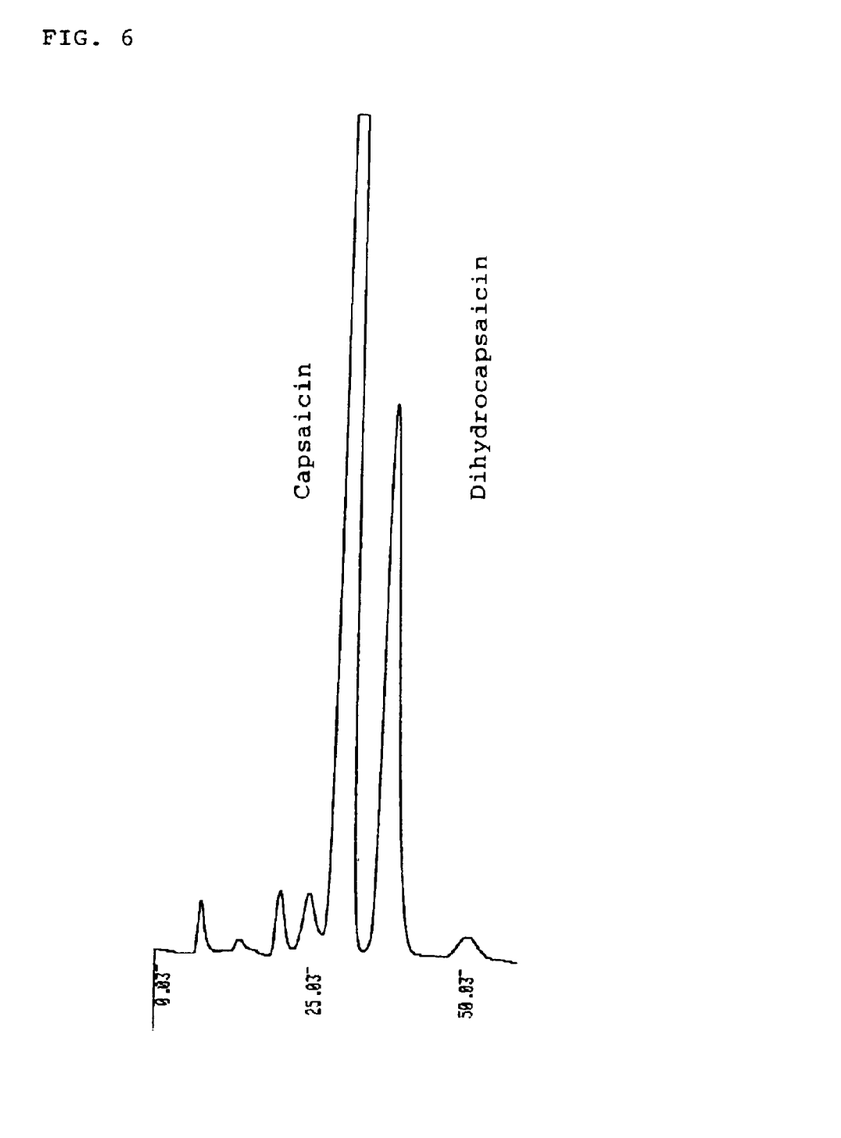
FIG. 6 is a chromatogram in the case of separation of the sample used in Example 2 by one parallel column of the present method.
Figure 7:
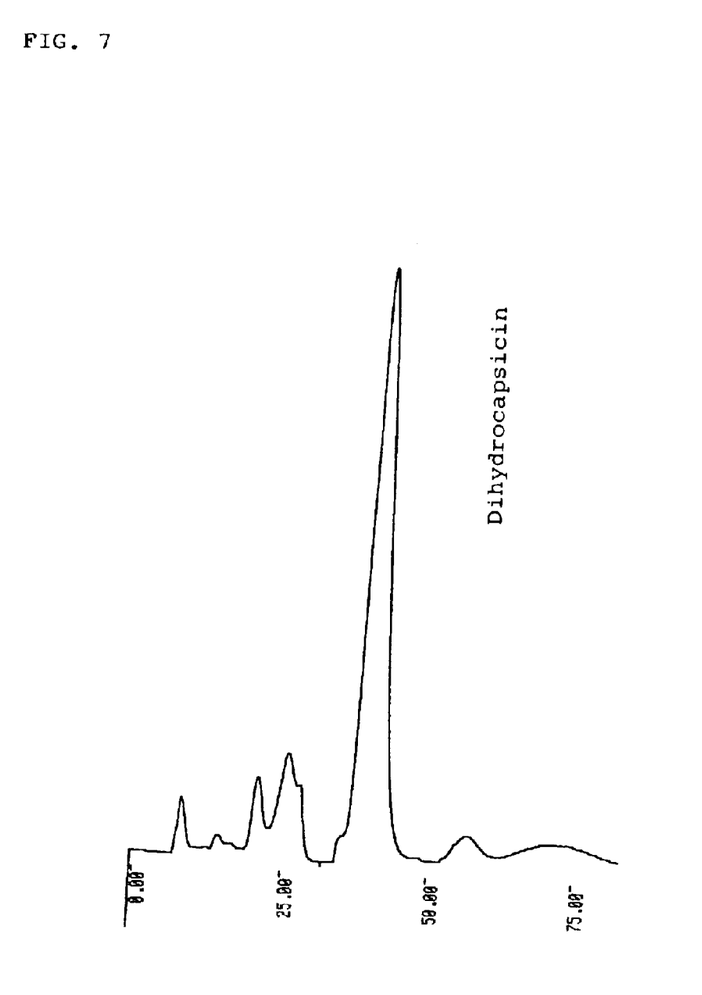
FIG. 7 is a chromatogram of the separation, in the same way as for FIG. 6, of the residue after only the capsaicin containing peak from the example of FIG. 6 is guided to the serial columns.
Figure 8:
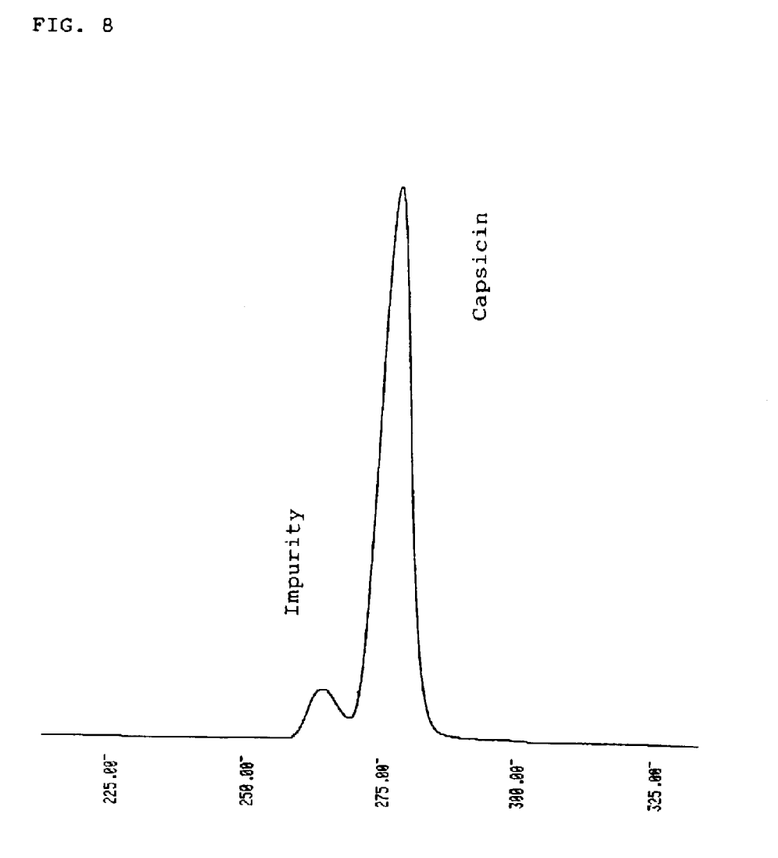
FIG. 8 is a chromatogram when the capsaicin peak guided to the serial columns in FIG. 7 is separate d and purified.

A chromatogram when separating this sample by using one parallel column is shown in FIG. 6. When measuring a chromatogram of the residue separated after guiding the capsaicin-containing peak to the serial columns, the chromatogram of FIG. 7, in which the capsaicin-containing peak had been removed from FIG. 6, was obtained. When the capsaicin-containing peak was further separated on the 10 serial columns, as shown in FIG. 8 a small impurity peak was separated before the capsaicin peak. A separation efficiency of about 10,000 plates was obtained in this example.

Figure 9:
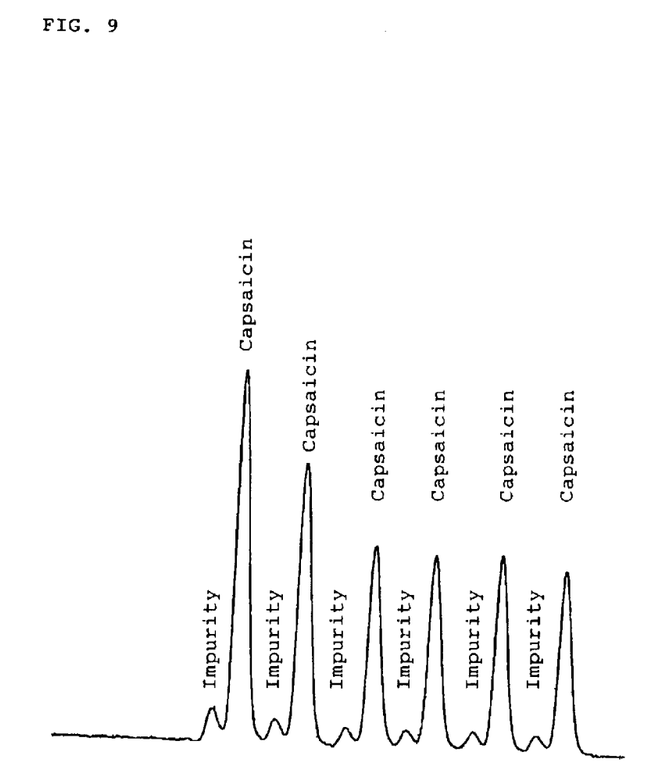
FIG. 9 is an example of a separation, by the present method, of capsaicin from a crude red chilli pepper extract.
Figure 10:
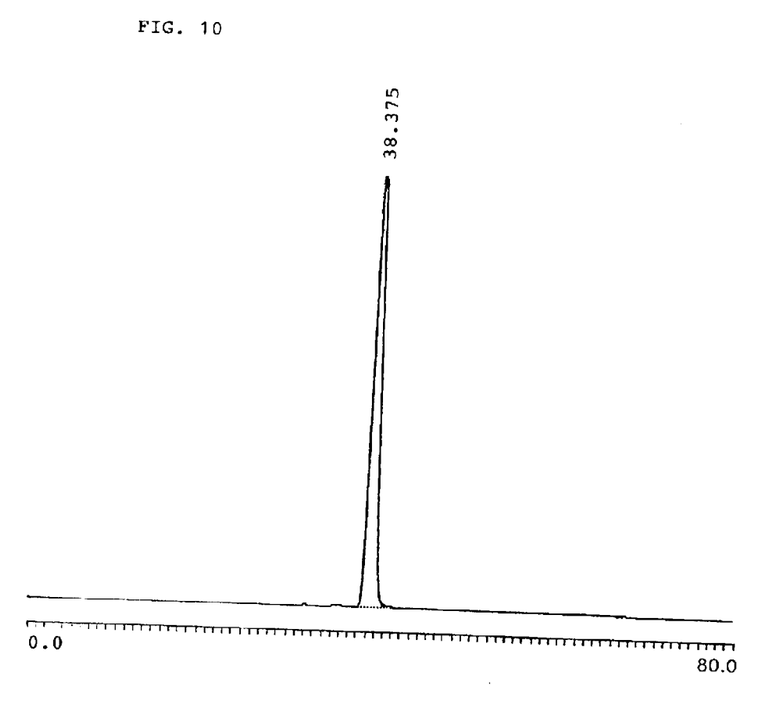
FIG. 10 is a chromatogram of an analysis of the capsaicin fraction separated and purified in FIG. 9

A chromatogram when separating by this system injecting the sample 6 times at intervals of 30.7 min is shown in FIG. 9. The eluate was further fractionated by means of a fraction collector, the capsaicin fractions corresponding to the larger peaks were collected, and when these fractions were analyzed by liquid chromatography in the same way, as shown in FIG. 10, since apart from the shock at the time of sample injection no other peak than capsaicin was observed, it was found that capsaicin was separated with good purity.

Specifically, the area purities when the shock part was added and not added were greater than 99.8% and greater than 99.9% respectively, and a purity higher than commercial high purity grade reagent was obtained. Therefore, by improving pre-processing of the sample, an area purity of 99.99% will be obtained.

It the eluant is appropriately replenished in the present method sample injection and separation can be carried out continuously until all the sample solution has gone. The sample injection frequency shown in the present example is only an embodiment, and the sample injection frequency is not limited to 6 cycles. Injection of the sample can be carried out continuously as long as the performance of the column a packing material does not deteriorate. Furthermore, in a case where the performance is reduced, or in a case where the separation is insufficient, it is naturally possible to increase the number of columns of a serial column system appropriately to obtain the target resolution.

Effects of the Invention

As described above, in accordance with the system or method of the present invention, by attempting to eliminate as far as possible parts of the packing material where no sample is present and utilize the packing material effectively, and at the same time as increasing the amount processed per unit of a pacing material in preparative chromatography eliminating as far as possible parts that are not related to separation within the system, which are drawbacks of chromatography using a column, the amount processed per unit time and per unit of mobile phase solvent can be increased. As a result, in accordance with the system or method of the present invention, an efficient separation operation is possible with a smaller scale system and at a lower cost than before.

Therefore, since the present invention is particularly effective in, for example, the purification of pharmaceutical materials with high biological activity, or intermediate compounds for synthetic research, it can be applied to the pharmaceutical industry, etc.

What is claimed is:

1. A chromatography system comprising three or more column units arranged in parallel, wherein outlets from which fractions are taken out are connected to the same flow path.

2. The system according to claim 1 wherein the column unit connected to the downstream side of each of the column units arranged in parallel comprises three or more column units linked in series with each other.

3. The system according to claim 2 wherein the column units linked in series with each other consist of 10 or more column units.

4. The system according to claim 3, wherein the injection inlet of each of the column units arranged in parallel is connected to the same supply flow path.

5. The system according to claim 2, wherein the injection inlet of each of the column units arranged in parallel is connected to the same supply flow path.

6. The system according to claim 2 further comprising a valve and a pump having, between columns of the column units linked in series and purifying the target component, a flow path system for removing separated impurities and a flow path system for introducing a pure mobile phase corresponding to the volume of the mobile phase removed.

7. The system according to claim 1, wherein the injection inlet of each of the column units arrange in parallel is connected to the same supply flow path.

8. The system according to claim 7 wherein a valve is provided in the supply flow path in order to inject a sample with a time interval between each of the column units arranged in parallel.

9. The system according to claim 1 further comprising a valve and a pump to enable the fractions taken out from each of the column units arranged in parallel to be sequentially introduced into the column unit connected to the downstream side thereof.

10. The system according to claim 9 wherein the valve and the pump that enable the fractions taken out from each of the column units arranged in parallel to be sequentially introduced into the column unit connected to the downstream side thereof carry out the introduction while maintaining a time interval in order that a peak of a purified target component and a peak of an impurity do not overlap in the column unit connected to the downstream side.

11. The system according to claim 1 further comprising a computer system that automatically controls one, two or more of sample injection, valve flow path switchover, and pump operation and stopping.

12. The system according to claim 1 wherein it is used for separation and purification of a biologically active material from a mixture containing the biologically active material.

13. The system according to claim 1, wherein the injection inlet of each of the column units arranged in parallel is connected to the same supply flow path.

* * * * *